(12) United States Patent
Schilowitz et al.

(10) Patent No.: US 7,109,729 B2
(45) Date of Patent: Sep. 19, 2006

(54) METHOD FOR ANALYSIS OF A WORKING FLUID USING IMPEDANCE SPECTROSCOPY

(75) Inventors: Alan Mark Schilowitz, Highland Park, NJ (US); Monica M. Lira-Cantu, Barcelona (ES); Limin Song, Princeton Junction, NJ (US); Walter David Vann, Marlton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/439,156

(22) Filed: May 15, 2003

(65) Prior Publication Data

US 2004/0085080 A1 May 6, 2004

Related U.S. Application Data

(60) Provisional application No. 60/387,056, filed on Jun. 7, 2002.

(51) Int. Cl.
G01R 27/08 (2006.01)
G01R 27/30 (2006.01)
G01R 27/00 (2006.01)

(52) U.S. Cl. ............... 324/698; 324/663; 702/65
(58) Field of Classification Search ........... 324/663, 324/698, 664, 691–697, 658–662; 702/65
See application file for complete search history.

(56) References Cited

U.S. PATENT DOCUMENTS

| 3,990,960 | A | 11/1976 | Ellison | 204/195 |
|---|---|---|---|---|
| 4,029,554 | A | 6/1977 | Ellison | 204/1 T |
| 5,296,843 | A | 3/1994 | Wohlstein et al. | 340/603 |
| 5,425,867 | A | 6/1995 | Dawson et al. | 204/400 |
| 5,489,849 | A | 2/1996 | Sadoway et al. | 324/447 |
| 5,523,692 | A | 6/1996 | Kuroyanagi et al. | 324/438 |
| 5,540,086 | A | 7/1996 | Park et al. | 73/53.05 |
| 5,691,701 | A | 11/1997 | Wohlstein et al. | 340/603 |
| 5,739,916 | A | 4/1998 | Englehaupt | 356/414 |
| 5,824,889 | A | 10/1998 | Park et al. | 73/116 |
| 5,900,810 | A | 5/1999 | Park et al. | 340/450.3 |
| 5,907,278 | A | 5/1999 | Park et al. | 340/450.3 |
| 5,929,754 | A | 7/1999 | Park et al. | 340/439 |
| 6,091,484 | A | 7/2000 | Venica et al. | 356/70 |
| 6,268,737 | B1 | 7/2001 | Marszalek | 324/663 |
| 6,577,112 | B1 * | 6/2003 | Lvovich et al. | 324/71.1 |

FOREIGN PATENT DOCUMENTS

| DE | 19741892 | 4/1999 |
|---|---|---|
| DE | 19757924 | 7/1999 |
| DE | 10100624 | 7/2001 |

(Continued)

OTHER PUBLICATIONS

Popkirov, et al—"Optimization of the Pertubation Signal for Electrochemical Impedance Spectroscopy in the Time Domain"— Nov. 1993— pp. 3111-3115— New York, US—#XP000955440.
Wang, et al—"The Application of A.C. Impedance Technique for Detecting Glycol Contamination in Engine Oil" — May 15, 1997 — pp. 193-197— Warren, Michigan, USA.

(Continued)

*Primary Examiner*—Anjan Deb
*Assistant Examiner*—Amy He
(74) *Attorney, Agent, or Firm*—James A. Zboray; Gary P. Katz

(57) ABSTRACT

An on-line method for determining the condition of low conductivity working fluids using alternating current, electro-impedance spectroscopy is provided by making measurements over a range of frequencies at temperatures at or above 50° C.

7 Claims, 4 Drawing Sheets

FOREIGN PATENT DOCUMENTS

| | | |
|---|---|---|
| EP | 1014082 | 6/2000 |
| EP | 1111383 | 6/2001 |
| FR | 2820824 | 2/2001 |
| WO | 9958965 | 11/1999 |

OTHER PUBLICATIONS

J. Ross Macdonald, editor. "Impedance Spectroscopy EmPhasizing Solid Materials and Systems", John Wiley & Sons, New York, 1987, pp. 4-6.

* cited by examiner

METHOD FOR ANALYSIS OF A WORKING FLUID USING IMPEDANCE SPECTROSCOPY

This application claims the benefit of U.S. Ser. No. 60/387,056 filed Jun. 7, 2002.

FIELD OF INVENTION

The present invention is broadly concerned with improvements in analyzing the electrical properties of a working fluid, such as a lubricating oil. More particularly the invention is concerned with an on-line, real time, electrical measure of lubricating oil degradation.

BACKGROUND OF INVENTION

Working fluids, such as lubricating oils and hydraulic fluids, are important components of a wide variety of mechanical systems in which they provide one or more functions such as lubricating moving parts, transferring force or energy on the mechanical system, protecting parts against wear or even a combination of these.

These fluids typically consist of a hydrocarbon, base oil formulated with numerous additives selected to enhance one or more performance characteristics of the fluid.

With use over time these fluids may become contaminated with substances with which they come into contact, by the ingress of foreign substances in the mechanical system, by oxidation of the base oil and chemical decomposition of the additives used in the formulated fluids. The net result is a decrease in the performance characteristics of the fluid with the concomitant negative impact on the mechanical system using the fluid.

Therefore, in many industrial environments regular fluid analysis by common laboratory methods is a standard modus operandi. This necessitates running a sample of the fluid and transporting it, typically off-site, for analysis. This procedure normally takes at least three full days before the requisite analysis is completed and a report can be obtained. Such a time lag is highly undesirable.

The art is replete with proposed methods for the on-line evaluation of the quality of lubricants, many of which are based on electrical measurements, such as the dielectric constant or impedance of the fluid, with the measurements being taken most often at one, and sometimes two, discrete and fixed frequencies. Experience has shown, however, that these methods are not entirely satisfactory. For example, at some frequencies and at low temperatures the electrical property of the fluid being measured is insufficiently sensitive to give a reliable indication of the condition of the fluid and even if sufficiently sensitive, the frequency chosen may not necessarily provide an accurate indication of the condition of the lubricant. Also, the wires and other components used for making electrical measurements can produce spurious effects that obscure or distort the electrical properties of the fluid. Moreover, the best frequency for optimum sensitivity is highly dependent on the properties of the working fluid and measurements typically taken at discrete and fixed frequencies are not optimized for a specific working fluid.

Additionally, many working fluids have extremely low conductivities. For example, industrial oils typically have significantly lower conductivities than internal combustion engine lubricants undoubtedly due to the higher viscosity and lower additive concentrations of the industrial lubricants. Consequently the ability to employ electrical measurements based on fixed frequency measurements developed for engine lubricants to determine the quality or condition of that have relatively low conductivities such as industrial oils is quite problematic.

Thus there remains a need for improvements in determining the condition of a working fluid such as a lubricant.

An object, therefore, of the present invention is to provide a method for detecting the depletion of performance additives in a lubricant.

Another object is to provide an electrical measurement method for determining the condition of low conductivity industrial oil.

Still another object is to provide for improving the sensitivity in the electrical measurement for determining the condition of working fluids.

These and other objects will become apparent from the description which follows.

SUMMARY OF INVENTION

Briefly stated, the present invention employs alternating current (AC) electro-impedance spectroscopy to determine for working fluids such as lubricants, and especially industrial oils, one or more of the following properties: the resistance, the capacitance, the frequency at which the phase angle between the voltage and current is 45 degrees (Omega max), the time constant, and discrete impedance values; and comparing the determined property with a predetermined value for the same property for a known fluid condition to determine the condition of the working fluid. Preferably the property determined is measured at a temperature above about 50° C.

DETAILED DESCRIPTION OF INVENTION

AC (alternating current) electro-impedance spectroscopy is a well known technique. It involves the imposition of AC signals over a broad range of frequencies to a material to be analyzed. The electrical response to those signals is determined and by the application of electrical circuit theory a description of the properties of the material is obtained.

The present invention employs AC electro-impedance spectroscopy to determine the conditions of a working fluid. Indeed the present invention is particularly applicable to determining the conditions of low conductivity oils. The low conductivity oils to which the present invention is particularly applicable are those unused oils that have a kinematic viscosity at 100° C. of greater than 15 cSt and containing less than about 3 wt % (active basis) of additives selected from dispersants, antioxidants, detergents, VI improvers and antiwear agents. Thus, an important aspect of the present invention is the provision of an AC electro-impedance spectroscopic method for determining the condition of industrial oils, especially on-line, i.e., when contained in mechanical systems, even when the systems are operating.

Figure 1:
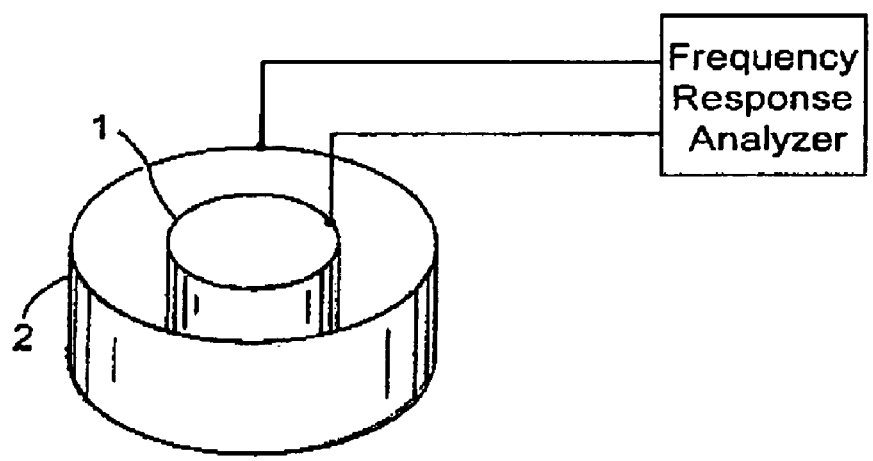
FIG. 1 is a schematic illustration of a measuring device for collecting impedance data according to the invention.

According to the invention, a pair of spaced apart electrodes, such as the concentric, cylindrical electrodes 1 and 2 shown in FIG. 1, are placed in a body of working fluid to be analyzed. Preferably the working fluid is within a mechanical system, for example in an oil reservoir or sump of a mechanical system (not shown), in an oil delivery manifold, or bypass manifold of a mechanical system (also not shown) requiring lubrication or use of a working fluid.

The dimensions of the electrode, of course, will depend on its positioning with the mechanical system and the nature of the working fluid being analyzed. For industrial lubricants, such as paper machine oils, the length of the electrodes shown in FIG. 1 typically will be in the range of between about 0.5 cm to about 20 cm, the diameter of the outer electrode between about 0.5 cm to about 4 cm and the gap between the inner and outer electrode between about 0.1 to 10 mm. Other geometries for the electrodes may be employed, such as flat parallel plates, flat interdigitated electrodes etched on an inert substrate and the like.

Placing the electrodes in a working fluid contained in a mechanical system permits on-line, real time, analysis of the fluid, i.e., the condition of the fluid can be measured continuously while employed in the mechanical system without the need to remove a sample of the fluid from the system for analysis.

An AC signal is applied to one electrode at a plurality of frequencies, typically at more than three frequencies, for example from 4 to 1000 frequencies and preferably from 4 to 20 in the range of from 1 Hz to 3M Hz. The applied signal produces an electrical output at the other electrode which is measured. A device for applying the signal and measuring the output, i.e., a frequency response analyzer (FRA) is shown diagrammatically in FIG. 1 by reference numeral 3. Such frequency response analyzers are commercially available and are used to acquire frequency dependent impedance data. Another fluid impedance monitor is shown schematically in FIG. 2 where 1 and 2 represent concentric electrodes immersed in an oil 4. A digital function generator 5 generates a predetermined discrete sequence of signals and a digital-to-analog converter 6 converts the sequence to an analog sinusoidal voltage of small amplitude, Vn, and frequency, $\omega$, and applies the voltage to the outer electrode 2. The applied signal produces an electrical charge on the inner electrode 1. A charge amplifier 7 converts the charge into a sinusoidal voltage, Vout, at the same frequency, $\omega$. The time-based waveforms of both input and output voltages are converted by an analog-to-digital converter 8 and the resulting data is acquired and processed by data processor 9.

In the data processor 9, a digital frequency response analyzer is used to obtain the complex transfer function of the output voltage with respect to the input voltage, i.e., the ratio of the complex amplitude of the sinusoidal output voltage to that of the sinusoidal input voltage. This complex transfer function is equal to the ratio of the feedback impedance of the charge amplifier 7 to the impedance of the working fluid to be analyzed. Dividing the transfer function by the known amplifier feedback impedance, the admittance of the working fluid is obtained. The reciprocal of the admittance is equal to the impedance of the working fluid. This process of data acquisition and processing is repeated over all operating frequencies until the desired impedance or admittance spectrum data is obtained.

According to the invention the frequency dependent impedance or admittance data obtained as described herein is used to determine one or more of the resistance, the capacitance, the frequency at which the phase angle between the voltage and current is 45° (Omega max), the time constant of the working fluid. This can be achieved, for example, by plotting the frequency dependent impedance data in the form of a Nyquist plot where, in rectangular coordinates, imaginary impedance ($Z''=\text{im}(Z)=[Z]\sin(\Theta)$) is plotted against real impedance ($Z'=\text{re}(Z)=[Z]\cos(\Theta)$) or, in polar coordinates, $|Z|=[(Z')^2+(Z'')^2]^{1/2}$ is plotted against $\Theta$, the phase difference between voltage and current. Examples of Nyquist plots are shown in FIG. 3 for a paper machine lubricant.

Figure 3:
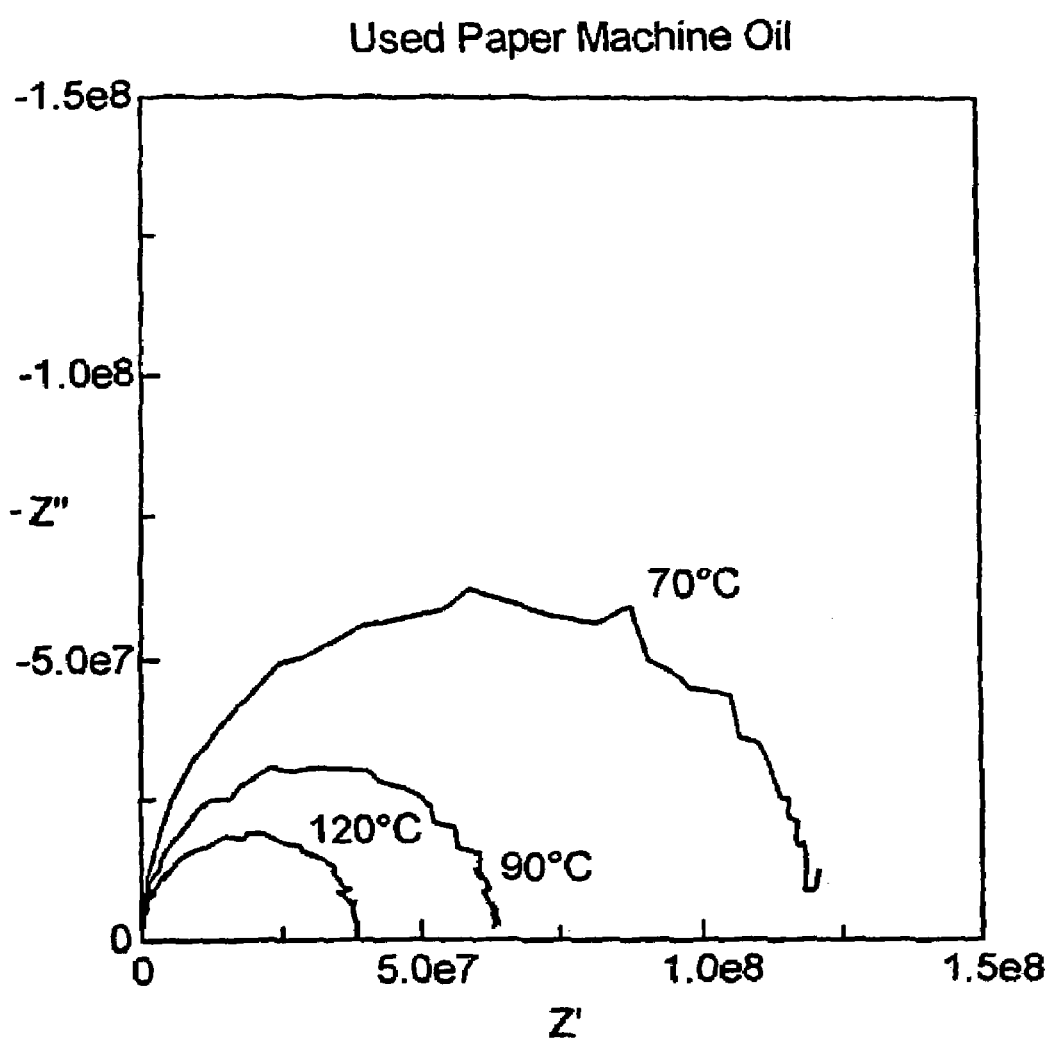
FIGS. 3 and 4 demonstrate the ability to generate Nyquist curves for low conductivity oils at temperatures above 50° C.

In FIG. 3, the Y axis is the negative of the imaginary part of impedance, $Z''$ and the x axis is the real part of impedance, $Z'$.

Preferably the Nyquist plot impedance data is further analyzed by fitting the data to a least-squares best fit curve. Such a curve can be fit using many standard data analysis packages. The resistance of the oil/electrode system can then be calculated by determining the diameter of the curve along the x axis. The frequency at which $\Theta$ reaches 45 degrees is known as Omega max. The reciprocal of Omega max is the time constant, RC. The capacitance may then be determined using relations, Omega max=1/RC.

In one embodiment of the invention frequency dependent impedance data are measured for more than 4 values of $\Theta$ spanning a range of at least 45 degrees and a partial Nyquist curve is constructed from that data. This portion of the curve can then be analyzed with a standard least squares fitting program by assuming that the Nyquist plot follows an elliptical curve. The entire Nyquist curve can then be constructed by extrapolating to $\Theta$ values of zero and 180 degrees. At the same time values for capacitance, resistance and Omega max can also be determined.

At least one of the resistance, capacitance, Omega max, time constant and impedance values obtained for the working fluid is then compared to a predetermined value to determine the condition of the fluid being analyzed or monitored.

Preferably, the AC elecro-impedance measurements made on low conductivity industrial oils are made at a temperature above about 50° C. and more preferably above about 65° C. and up to about 150° C.

Figure 2:
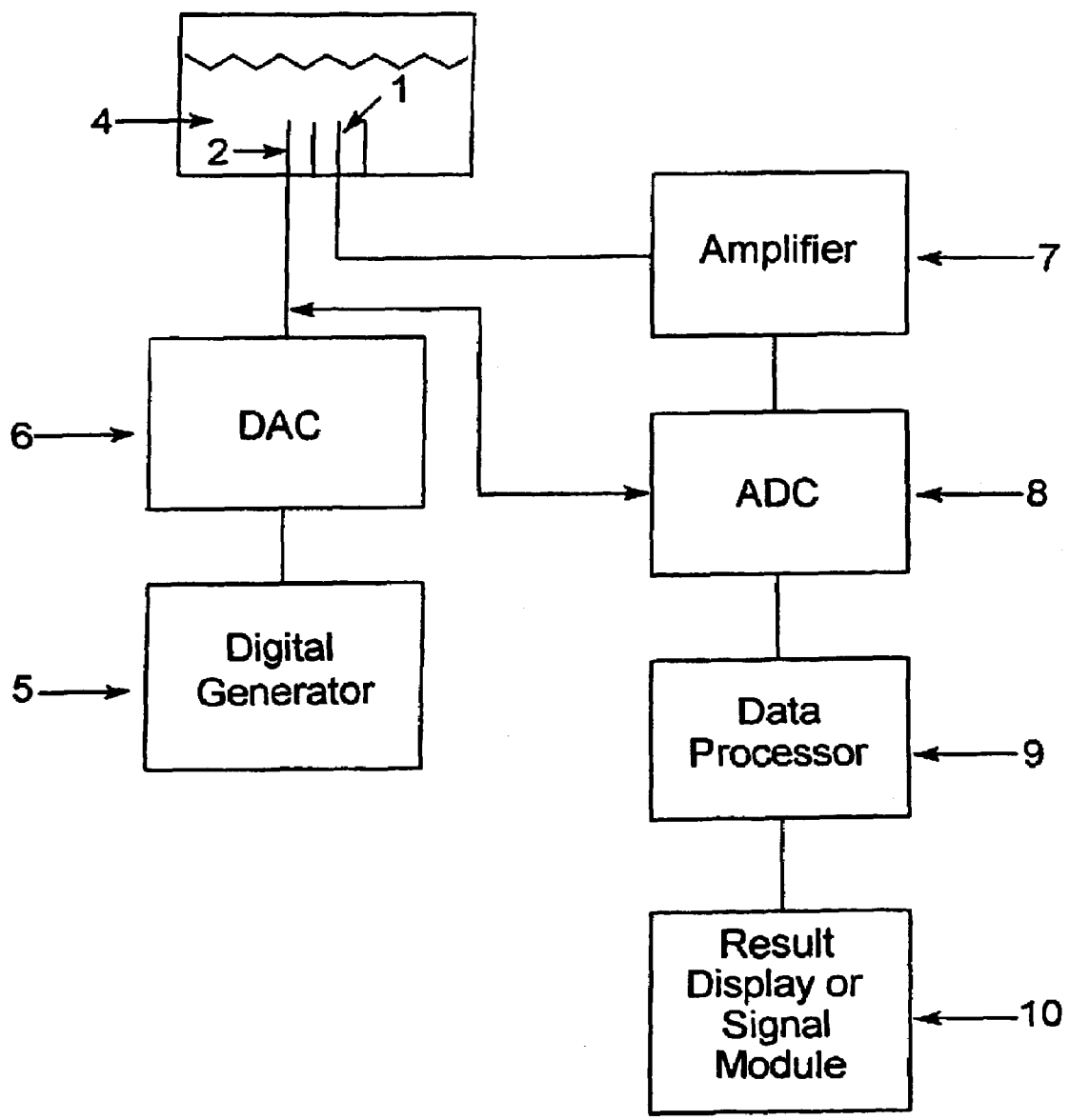
FIG. 2 is a schematic illustration of a system for monitoring the condition of a working fluid according to the invention.

In one embodiment the on-line, real time, impedance measurements taken and used to calculate at least one of the resistance, capacitance, Omega max, time constant and discrete impedance values of a working fluid and compared to a predetermined similar value or values as the case may be, is used to provide a visual display such as an indication of the remaining useful life of the fluid. Alternatively, a visual or other signal such as a bell or alarm may be provided when the fluid condition reaches a predetermined state requiring changing of the fluid before continuing operating the mechanical system. This is shown in FIG. 2 as result display or signal module 10.

EXAMPLES

Example 1

A used sample of a commercial paper machine oil was subjected to AC electroimpedence measurement at 70° C., 90° C. and 120° C. using a Solartron 1260 frequency response analyzer (FRA), an AC amplitude of 1 volt and a DC offset of 5 volts. Frequency was scanned from 10 Hz to 3.2 MHz. FIG. 3 shows the Nyquist curves generated from the data.

Example 2

Figure 4:
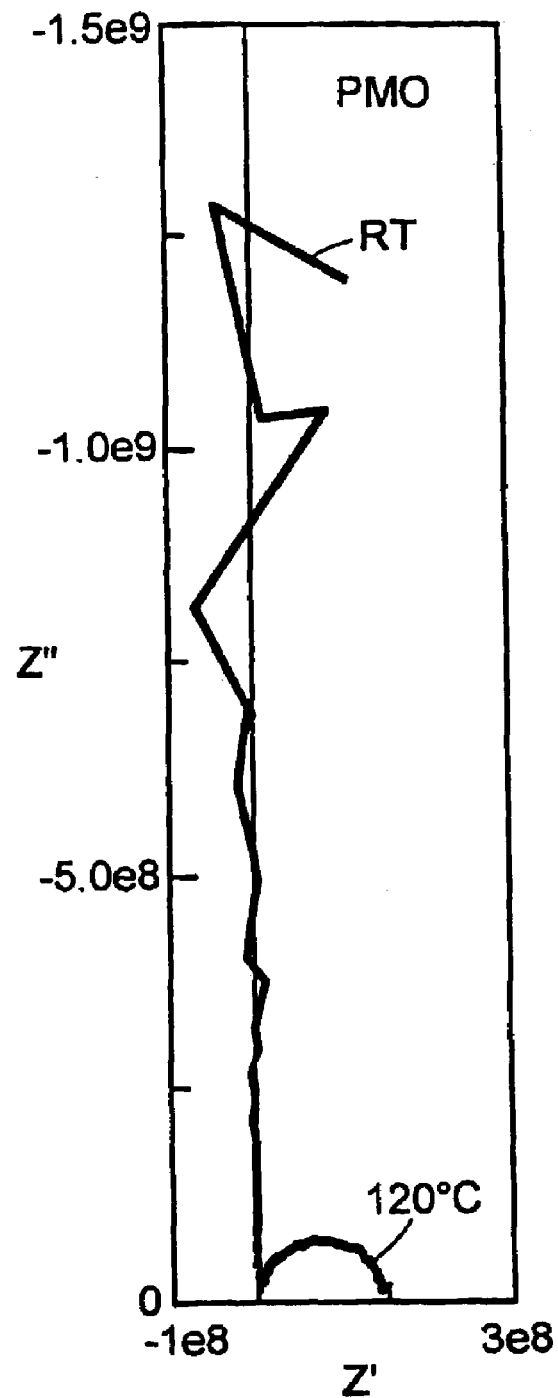

Following the procedure of Example 1 a fresh sample of the same commercial paper machine oil of Example 1 was measured at room temperature (about 25° C.) and at 120° C. FIG. 4 shows that a Nyqist curve could not be generated when the measurement was made at room temperature.

Example 3

Ten samples of a paper machine oil were obtained from operating paper machines and their impedance was measured at 130 frequencies at 120° C. over a range of 10 hertz to 3.2 megahertz using a Solartron Model 1260A impedance/gain phase analyzer and a Kavlico cylindrical impedance electrode pair with the oscillator and output circuitry disconnected. The resulting Nyquist curve was fit using Zplot/Zview software from Scribner Associates. The resistance was then calculated. In addition, the samples were analyzed by inductively coupled plasma (ICP) spectroscopy for phosphorous, zinc and calcium, important elements found in paper machine oil additive packages.

Depletion of these elements results in poor lubricant performance and is indicative of loss or degradation of the additives. The data are summarized in Table 1.

TABLE 1

| Sample No. | Resistance | P (ppm) | Zn (ppm) | Ca (ppm) |
|---|---|---|---|---|
| 1 | 11.48 | 482 | 752 | 110 |
| 2 | 8.0 | 477 | 717 | 143 |
| 3 | 13.55 | 515 | 744 | 270 |
| 4 | 11.98 | 482 | 733 | 263 |
| 5 | 9.39 | 519 | 804 | 154 |
| 6 | 11.70 | 521 | 819 | 178 |
| 7 | 14.29 | 514 | 802 | 186 |
| 8 | 10.11 | 524 | 836 | 193 |
| 9 | 35.55 | 444 | 614 | 101 |
| 10 | 28.48 | 256 | 192 | 24 |

The data demonstrate that resistance, as measured in accordance with the present invention, is indicative of additive level. Note especially the very high resistance and low additive levels of samples 9 and 10.

What is claimed is:

1. A method for determining the condition of a working fluid contained in a mechanical system and at a temperature above about 50° C. which comprises:
   disposing a pair of spaced apart electrodes in the fluid;
   imposing an AC signal over a range of 4 or more frequencies on the electrodes;
   determining the impedance or admittance data as a function of the frequencies from electrical response to the imposed AC signals;
   determining at least one of the following properties: resistance, capacitance, Omega max, and time constant by plotting the frequency dependent impedance data in the form of a Nyquist plot by fitting the data to a curve where, in rectangular coordinates, imaginary impedance (Z") is plotted against real impedance (Z') or, in polar coordinates, $Z=[(Z')^2(Z")^2]^{1/2}$ is plotted against $\Theta$, the phase difference between voltage and current, wherein said resistance, capacitance, Omega max, and time constant is calculated by determining the diameter of the curve; and
   comparing one of the properties determined to a predetermined value of the said properties whereby an indication of the condition of the fluid is determined.

2. The method of claim 1 wherein the frequencies range between 1 and 10,000 Hz.

3. The method of claims 1 or 2 including providing an electrical signal indicative of the fluid condition.

4. A method for obtaining an indication of the performance additive levels of a industrial oil containing less than about 3 wt % performance additives, on active ingredient basis, where the oil is contained in a mechanical system comprising:
   measuring the impedance data of the oil at a plurality and over a range of frequencies while the oil is contained in the mechanical system and is at 500° C. or higher;
   obtaining a value for at least one of resistance, capacitance, Omega max, and time constant from the impedance data by plotting the frequency dependent impedance data in the form of a Nyquist plot by fitting the data to a curve where, in rectangular coordinates, imaginary impedance (Z") is plotted against real impedance (Z') or, in polar coordinates, $Z=[(Z')^2+(Z")^2]^{1/2}$ is plotted against $\Theta$, the phase difference between voltage and current, wherein said resistance, capacitance, Omega max, and time constant is calculated by determining the diameter of the curve; and
   comparing the obtained value or values with a value or values for a known additive level whereby an indication of the additive level is obtained.

5. The method of claim 4 wherein the impedance data is measured by imposing an AC signal over a range of frequencies and the response to those signals is detected.

6. The method of claim 5 wherein the impedance data is measure at 4 or more frequencies in the range of between 1 and 10,000 Hz.

7. The method of claim 6 including means for generating an electrical signal when the obtained value exceeds a predetermined value.

* * * * *